United States Patent [19]
Elseviers et al.

[11] Patent Number: 6,018,034
[45] Date of Patent: Jan. 25, 2000

[54] PROCESS FOR THE PRODUCTION OF 2-KETO-D-GLUSONIC ACID

[75] Inventors: Myriam Elseviers, Kampenhout; Sonia Marianne Jeannine Coomans, Vilvoorde; Hilde Odile Jozefine Lemmens, Kontich; Harald Wilhelm Walter Röper, Brussels, all of Belgium

[73] Assignee: Cerestar Holdings B.V., Netherlands

[21] Appl. No.: 09/047,458

[22] Filed: Mar. 25, 1998

[30] Foreign Application Priority Data

Mar. 25, 1997 [GB] United Kingdom .................... 9706134

[51] Int. Cl.⁷ ....................................................... C07H 1/00
[52] U.S. Cl. ............................................ 536/18.5; 536/124
[58] Field of Search ..................... 536/18.5, 124

[56] References Cited

U.S. PATENT DOCUMENTS

| | | | |
|---|---|---|---|
| 4,212,988 | 7/1980 | Andrews | 560/174 |
| 4,242,145 | 12/1980 | Muller . | |
| 4,599,446 | 7/1986 | Kiyoura | 562/527 |
| 4,620,034 | 10/1986 | Smits | 562/531 |
| 4,843,173 | 6/1989 | Saito . | |
| 4,845,208 | 7/1989 | Fuertes et al. | 536/124 |
| 5,132,452 | 7/1992 | Deller et al. | 562/531 |

FOREIGN PATENT DOCUMENTS

| | | |
|---|---|---|
| 0 142 725 A1 | 5/1985 | European Pat. Off. . |
| 0 151 798 A2 | 8/1985 | European Pat. Off. . |
| 0 350 741 A1 | 1/1990 | European Pat. Off. . |
| 29 03 388 | 9/1979 | Germany . |
| 3823301 | 11/1989 | Germany . |
| 62-269745 | 11/1987 | Japan . |

OTHER PUBLICATIONS

Gallezot, Pierre "Selective Oxidation with air on metal catalysts", *Catal. Today,* vol. 37(4):405–418, 1997.

Besson et al. "Oxidation of glucose and gluconate on Pt, Pt Bi and Pt Au catalysts" *Recl. Trav. Chim. Pays—Bas* vol. 115(4):217–221, 1996.

*Primary Examiner*—Howard C. Lee
*Attorney, Agent, or Firm*—Pillsbury Madison & Sutro LLP

[57] ABSTRACT

This process for the production of 2-keto-D-gluconic acid starts from D-glucose. D-glucose is catalytically oxidised using molecular oxygen in a one-pot process. The oxidation is performed in the presence of well-known Pt/Pb catalysts. The initial reaction to D-gluconic acid is performed at constant pH between 7 and 10. There after the reaction is continued without pH control. This process results in a high selectivity compared with known processes.

12 Claims, 2 Drawing Sheets

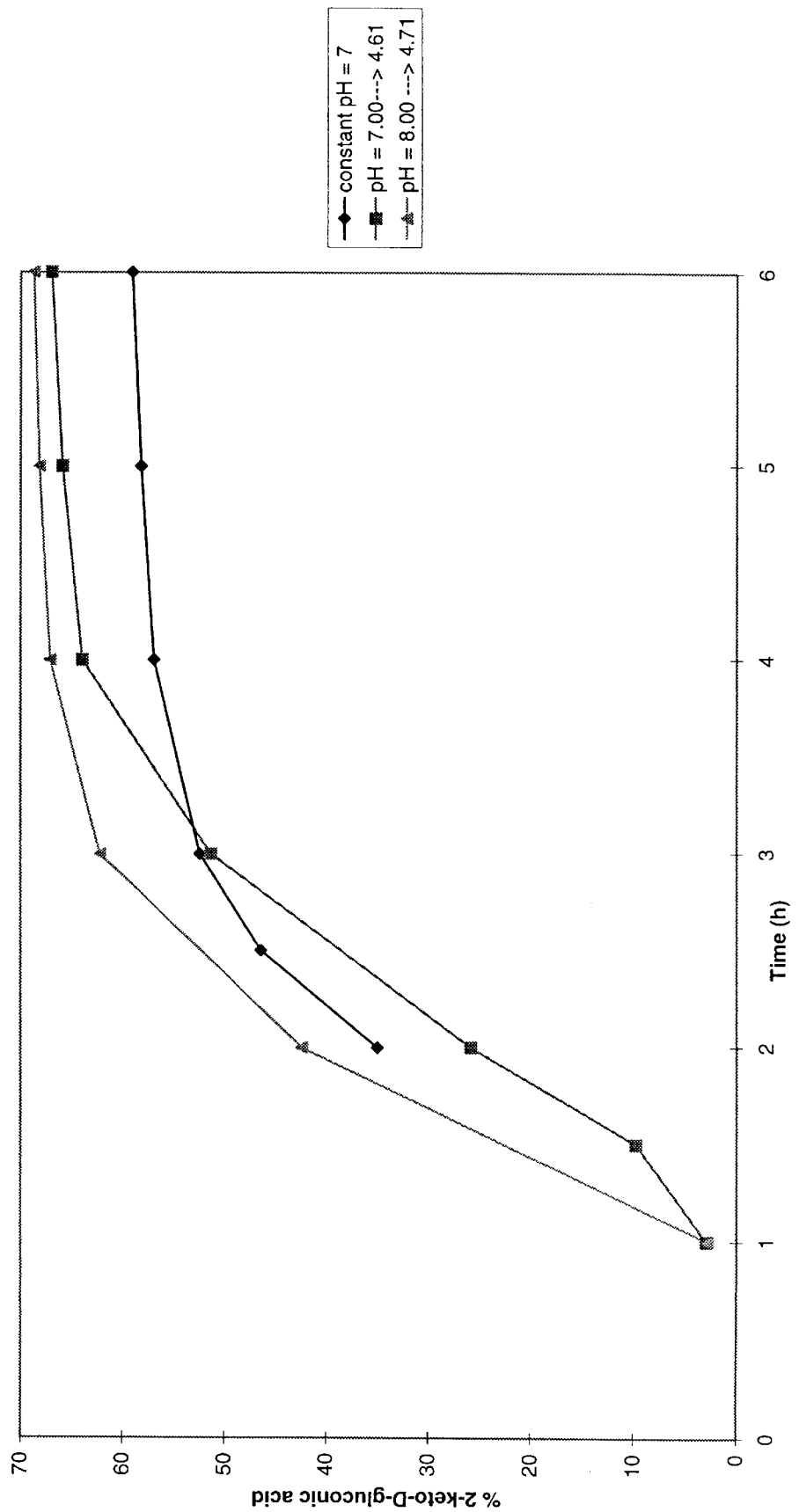
Figure 1: Influence of pH.
Production of 2-keto-D-gluconic acid

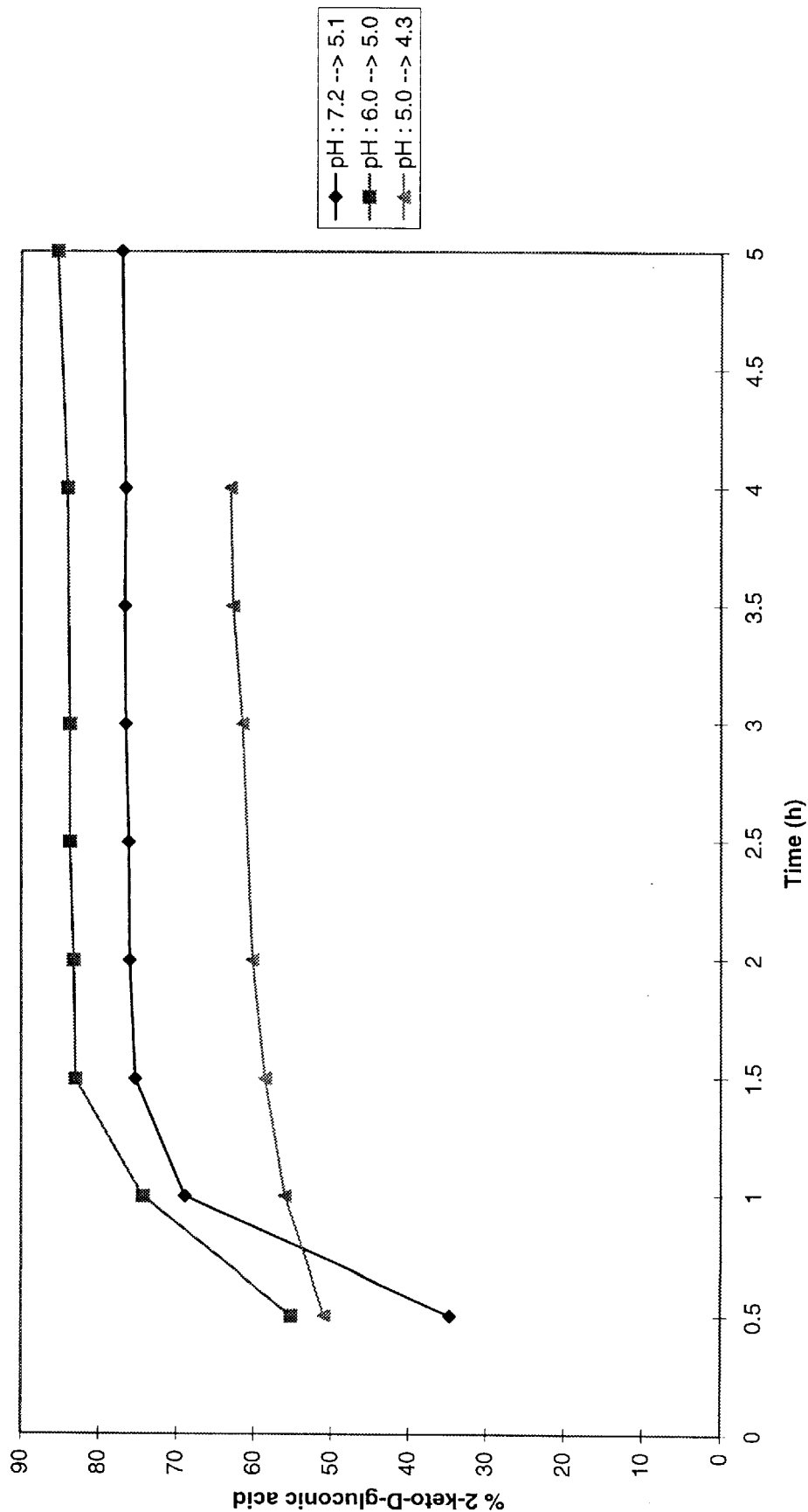

PROCESS FOR THE PRODUCTION OF 2-KETO-D-GLUSONIC ACID

TECHNICAL FIELD

The present invention discloses a method of producing 2-keto-D-gluconic acid. Specifically, the present invention relates to a method of producing 2-keto-D-gluconic acid from D-glucose consisting of a one-pot reaction. D-glucose is oxidised in situ to the intermediate D-gluconic acid, which in turn is further oxidised to 2-keto-D-gluconic acid.

BACKGROUND OF THE INVENTION 2-keto-D-gluconic acid can be prepared from D-glucose by fermentation, usually several subsequent fermentation steps are required. According to U.S. Pat. No. 4,879,229, U.S. Pat. No. 5,134,077, U.S. Pat. No. 5,234,819 and DE 42 38 905, D-glucose is fermented to 2,5-diketo-gluconic acid by micro-organisms of the genus Erwinia. According to U.S. Pat. No. 843,946 the obtained product is reduced by sodium hydride to a mixture of 2-keto-D-gluconic acid and 2-keto-L-gulonic acid. U.S. Pat. No. 4,180,511 describes a method to further improve the above-mentioned reduction. The main disadvantage of this process is the use of sodium hydride to perform the reduction, thus demanding heavily controlled reaction procedures. Moreover, the final products; 2-keto-L-gulonic acid and 2-keto-D-gluconic acid are obtained in quasi-equimolar amounts, thereby bringing the reaction efficiency to a theoretical maximum of about 50%.

U.S. Pat. No. 3,282,795 and D. Bull (Biotechnology and Bioengineering Vol. XXIII (1981) 373–389) describe the direct fermentative conversion of D-glucose into 2-keto-D-gluconic acid by *Serratia marcescens*, giving conversion rates as high as 95–100%. However, these conventional fermentation processes have disadvantages in that the volume of the fermentor is large and that the production costs are rather high.

EP 0 042 221 and J. Geigert (Carb. Res 113, (1983) 163–165) describe the enzymatic oxidation of D-glucose to D-glucosone by pyranose-2-oxidase followed by an enzymatic oxidation by D-glucose-1-oxidase to convert D-glucosone into 2-keto-D-gluconic acid. Although the conversion of D-glucosone into 2-keto-D-gluconic acid is nearly quantitative, the overall process is producing 2 moles of hydrogen peroxide per mole of 2-keto-D-gluconic acid. This excess of hydrogen peroxide has to be destroyed by catalase to avoid destruction of the enzyme and degradation of the reaction product This co-processing requires a lot of efforts and is adding up to processing costs.

Chemical oxidation of D-gluconic acid derivatives to 2-keto-D-gluconic acid gives, according to U.S. Pat. No. 2,153,311 low yields (40%) in the presence of chromic acid and iron sulphate as co-catalyst. Long reaction times (12 hours to 3 days) and high amounts of salts are the major drawbacks of this method.

According to U.S. Pat. No. 4,620,034 and EP 0 151 498, it is possible to apply catalytic oxidation to obtain 2-keto-D-gluconic acid from D-glucose or D-gluconic acid. Molecular oxygen is applied in the presence of a platinum-based catalyst, which is doped with lead or bismuth. Within 7–10 minutes 73 and 87% of 2-keto-D-gluconic acid, starting from D-glucose and D-gluconic acid, respectively are obtained. However, a slight increase in the reaction time (a few minutes) results in a dramatic drop of the yield of 2-keto-D-gluconic acid. It is not mentioned how to avoid this rapid degradation while at the same time maintaining the high yields of 2-keto-D-gluconic acid. It is not indicated what type of working-up procedure is to be used in order to avoid the degradation of 2-keto-D-gluconic acid into mainly oxalic acid. Moreover, the reaction time is very short and the required settings are too critical to set-up a reasonable large-scale process, since under the claimed reaction condition the product is very sensitive to degradation. Finally, the pH of the reaction medium is kept constant at pH=8 by the addition of alkali, preferably in the form of sodium hydroxide or a carbonate.

NL 9302127 describes the conversion of an aldonic acid to a 2-keto-aldonic acid which is also disclosed in EP 0 151 498. It indicates that the pH during the oxidation should be between 3 and 6.9 and that in a preferred embodiment the pH is not regulated and thus allowed to drop during the course of the reaction. 2-keto-D-gluconic acid, has a variety of commercial uses. In the form of the calcium salt, it is used in photography, mainly in developer formulations. It can also readily be converted into other commercially useful products such as furfural, D-arabinose, D-ribulose, and iso-ascorbic acid.

There exists a need for an economically feasible chemical process which gives high yields of 2-keto-D-gluconic acid within a reasonable reaction time and which maintains the amount of 2-keto-D-gluconic acid constant at high level and yet, has all the advantages of the catalytic oxidation process. The reaction time should be such that on an industrial scale the reaction can be worked-up within a reasonable timeframe without having the disadvantages of loosing high amounts of the desired product. The present invention provides such a method.

SUMMARY OF THE INVENTION

The present invention relates to a method for producing 2-keto-D-gluconic acid by catalytic oxidation from readily available sources such as D-glucose in a one-pot process, which is proceeding in such a way that the obtained level of 2-keto-D-gluconic acid is kept high.

The present invention discloses a one-pot process for producing 2-keto-D-gluconic acid starting from D-glucose (anhydrous, monohydrate, high dextrose syrups (starch hydrolysates) by oxidation with molecular oxygen in the presence of a platinum based catalyst doped with lead or bismuth characterised in that the process comprises the following steps:

a) in situ preparation of D-gluconic acid with molecular oxygen gas by keeping the pH of the reaction medium at a constant value between 7 and 10, until all (near equimolar amounts) alkali (sodium hydroxide, potassium hydroxide, sodium carbonate etc.) is consumed, b) continuing the oxidation while at the same time allowing the pH to drop from the constant value under a) to a value below 6, preferably to 5 or below 5.

It is another aspect of the present invention that the 2-keto-D-gluconic acid is obtained with a high selectivity and that it is not readily degraded. Moreover, the 2-keto-D-gluconic acid is also readily converted to iso-ascorbic acid.

BRIEF DESCRIPTION OF THE FIGURES

FIG. 1 demonstrates the influence of the pH on the production of 2-keto-D-gluconic acid starting from D-glucose.

FIG. 2 demonstrates the influence of the pH on the production of 2-keto-D-gluconic acid starting from D-gluconic acid.

DETAILED DESCRIPTION OF THE INVENTION

The present invention can be summarised as follows. The invention discloses the catalytic oxidation of D-glucose with molecular oxygen in the presence of a platinum based catalyst doped with lead or bismuth. During the process of the present invention mild reaction conditions are applied with respect to temperature, oxygen gas pressure and catalyst concentration, this results in good yields of 2-keto-D-gluconic acid especially when allowing a pH drop during the course of the reaction to a final value of pH 5.0 or below 5.0.

More specifically the present invention discloses a one-pot process for producing 2-keto-D-gluconic acid starting from D-glucose by oxidation with molecular oxygen in the presence of a platinum based catalyst doped with lead or bismuth characterised in that the method comprises the following steps:

a) in situ preparation of D-gluconic acid with molecular oxygen gas by keeping the pH of the reaction medium at a constant value between 7 and 10, until all (near equimolar amounts) alkali is consumed, b) continuing the oxidation while at the same time allowing the pH to drop from the constant value under a) to a value below 6, preferably to 5 or below 5.

The D-glucose, which is used in the present process may be in the form of anhydrous D-glucose or as D-glucose monohydrate. It is also possible to use a high dextrose syrup (starch hydrolysate).

The first step is allowed to proceed at a constant pH value between 7 and 10 preferably between 8 and 9. The pH is kept constant by automatic addition of alkali. This alkali can be in different forms. Generally metal hydroxides or metal carbonates are used such as sodium hydroxide, potassium hydroxide, sodium carbonate.

The alkali is added until the amount is equimolar to the D-glucose. It is understood that small deviations from equimolarity (up to 10%) are acceptable. After this the addition of alkali is stopped and at the same time the reaction is allowed to proceed. Ending of the addition of the alkali results in a drop of the pH which leads to more favourable reaction conditions for the subsequent oxidation resulting in a much higher yield of the 2-keto-D-gluconic acid.

The pH is allowed to drop below 6, preferably below 5. It is advantageous to allow the pH not to drop too much below 5. If this nevertheless occurs alkali addition is resumed to keep the pH constant again at a desired value.

Stopping the addition of the alkali after the amount added is near equimolar with the glucose is essential. If the added amount is too low or if the addition of alkali is continued the yield of the 2-keto-D-gluconic acid will be below optimal.

The process for preparing the catalyst is known for example from EP 0 151 498. The platinum/lead catalyst is prepared by a precipitation of lead salts onto the platinum based catalyst. The ratio Pt to Pb is between 5:0.5 and 5:2.5 preferably between 5:1 and 5:2.

The process of the present invention can be performed between 0 and 200° C., generally the reaction temperature is in the range of 40° C. to 70° C., preferably between 50° C. and 60° C.

By comparative examples it is shown that dropping the pH during the course of the reaction is the essential point of this invention. The essential characteristic of this invention is the in situ preparation of D-gluconic acid, which occurs at high pH values (8–10), followed by the conversion to 2-keto-D-gluconic acid which occurs best at lower pH.

Another advantage of the present reaction conditions is that further degradation is avoided by dropping the pH during the course of the reaction. Comparative examples show that keeping the pH constant at high as well as at low values, results in much lower yields and selectivities towards 2-keto-D-gluconic acid. The fast degradation as described in U.S. Pat. No. 4,620,034 and EP 0 151 498 is not observed.

Example 1, which is representative of the present invention, shows that a high selectivity for the production of 2-keto-D-gluconic acid is obtained, when the reaction is started at pH 8, continued until an equimolar amount of alkali has been consumed and the pH is then allowed to drop to 5. The selectivity after 4 hours is still 87% and there is enough time to stop the reaction and work-up the product before it is degraded.

In Example 2 a slightly different catalyst is used and the pH is allowed to drop below 5 both aspects only slightly influence the selectivity. Examples 3 to 6 which are comparative examples illustrate that the selectivity of the present process is considerably lower if the pH is kept constant during the oxidation. This decrease is found at pH values of 5, 6 and 7. At pH 8 after 28 minutes there is hardly any 2-keto-D-gluconic acid detectable.

It is shown in Examples 7 to 9 that starting from D-glucose it is preferable to start at higher pH to prepare the intermediate, D-gluconic acid, and after equimolar consumption of alkali (sodium hydroxide, potassium hydroxide, sodium carbonate, etc.) a pH drop to 5.0 or below 5.0 is allowed, to obtain high yields of 2-keto-D-gluconic acid.

Examples 10 to 12 illustrate that with the ratio of Pt to Pb between 5:1 and 5:2.5 the selectivity of the reaction of the present invention is always above 80% with reaction times as long as 6 hours.

It is also shown that the selectivity of the reaction is dependent on the ratio of Pt to Pb and it is noticed that the preferred ratio of Pt to Pb is between 5:1.5 and 5:2.5.

Comparative Examples 13 and 14 used D-gluconic acid as starting material. It is shown again that there is an advantage in allowing the pH to drop during the reaction. From Examples 15 to 17 it can be concluded that it is advantageous to start at relatively high pH (6–7) and allow during the reaction the pH to drop to 5 or below 5.

The examples demonstrate that the lead content of the catalyst has an effect on the product yield and selectivity.

Although the examples are performed at low dry substance of the substrate, this is by no means a limiting step of the process. In practice the process is performed using much higher dry substance.

The advantage of this process in comparison with the earlier described catalytic oxidation such as disclosed in U.S. Pat. No. 4,620,034 and EP 0 151 498 is that the catalytic oxidation proceeds in such a way that the reached content of 2-keto-D-gluconic acid is kept constant without fast degradation to oxalic acid. Thereby the yield is optimal.

Furthermore, the time-frame and process of the reaction is such that it can easily be integrated into an industrial process. Whereas in the known process care has to be taken that the reaction is stopped in time and the time for stopping is critical since if one waits too long the yield will drastically decrease. The pH regulation is in the present invention ended after an equimolar amount is added. This amount can be calculated before the reaction is started and no measurement and adjustment of critical parameters is therefore required during the process.

Moreover during this process the free acid is prepared, which can directly be used for the conversion to iso-ascorbic acid. The product prepared according to U.S. Pat. No. 4,620,034 and EP 0 151 498 is obtained as a salt, requiring an additional conversion into the free acid before the lactonisation and enolisation into iso-ascorbic acid is possible. The invention is further illustrated by the following examples.

In the examples the method according to EP 0 151 498 and P. C. C. Smits in Carb. Res. 153 (1986) 227–235 has been applied to add the co-catalyst, lead or bismuth, to the platinum based catalysts. The content of the co-catalyst is changed by adding different amounts of lead or bismuth salts to the platinum based catalyst.

EXAMPLE 1

Catalytic Oxidation of D-glucose (1)
Preparation of the Catalyst
Ratio of Pt to Pb=5/2.

222.72 g wet Pt(5%)/C (44.9% d.s.) is suspended in 200 ml cold demineralised water. To the suspension 3.663 g lead (II) acetate $3H_2O$ is added. The suspension is heated until a small part of the water is evaporated, then allowed to cool to room temperature. After 18 hours of stirring, 69 ml of 1 M sodium hydroxide is added. The mixture is stirred for another 18 hours. The catalyst is collected and washed with demineralised water until the filtrate is neutral. The catalyst is dried at 50° C. under reduced pressure.
Catalytic Oxidation of D-glucose A D-glucose solution (5% d.s.) is heated at 55° C. under nitrogen, until no more oxygen is detected. The pH is brought to 8 by adding sodium carbonate. The catalyst, Pt/Pb/C, prepared as described above (ratio Pt to Pb=5/2) is added and the suspension is stirred at 1300 rpm for another 10 minutes under nitrogen. The reaction is started by switching from nitrogen to oxygen (maximum 10% oxygen in the mixture). During 1 hour equimolar amounts of 0.4 M sodium carbonate are consumed to keep the pH at 8. After 1 h the pH is no longer kept constant and no sodium carbonate is added until a pH of 5 is reached. From then on sodium carbonate is added again to keep the pH at 5. The amount consumed further corresponds with only 3% of equimolar amount.

The reaction medium is analysed by means of HPLC. D-glucose as well as the intermediate, D-gluconic acid, is qualified as unreacted product. The selectivity is expressed as the ratio of 2-keto-D-gluconic acid over 100 minus the unreacted product, thus taking into account all possible degradation products.

TABLE 1

| pH | Time (min) | 2-keto-D-gluconic | unreacted prod. | selectivity |
|---|---|---|---|---|
| 8.00 | 60 | 5.5 | 94.2 | 95.2 |
| 6.50 | 120 | 42.1 | 53.2 | 89.9 |
| 5.30 | 180 | 69.7 | 21.8 | 89.2 |
| 5.00 | 240 | 75.9 | 12.8 | 87.0 |

EXAMPLE 2

Catalytic Oxidation of D-glucose (2)
Preparation of Catalyst
Ratio of Pt to Pb=5/1.5

The catalyst Pt/Pb/C with the ratio Pt/Pb of 5/1.5 has been prepeared as described in example 1. 2.747 g lead (II) acetate $3H_2O$ is added to the suspension of 222.72 g Pt(5%)/C (44.9% d.s) in 200 ml cold demineralised water. The working-up is similar as described in example 1.
Catalytic Oxidation of D-glucose The catalyst Pt/Pb/C with Pt/Pb ratio of 5/1.5 is used, but the procedure is similar to the one described in example 1. Except that after adding equimolar amounts of 0.4 M sodium carbonate, the pH is dropped until finally a pH of 4.75 is reached. The reaction medium is analysed by means of HPLC as described in example 1.

TABLE 2

| pH | Time (min) | 2-keto-D-gluconic | unreacted prod. | selectivity |
|---|---|---|---|---|
| 8.00 | 48 | 3.0 | 96.7 | 91.6 |
| 5.38 | 120 | 56.1 | 35.0 | 86.4 |
| 4.90 | 180 | 70.1 | 18.6 | 86.1 |
| 4.80 | 240 | 71.7 | 16.7 | 86.0 |
| 4.77 | 300 | 72.2 | 16.0 | 86.0 |
| 4.75 | 360 | 72.2 | 15.6 | 85.6 |

EXAMPLES 3–6 (comparative)

Catalytic Oxidation of D-glucose at Constant pH
Example 3 pH=8

The catalyst Pt/Pb/C with Pt/Pb ratio of 5/1.5 is used. The D-glucose solution (5% d.s.) is heated at 55° C., pH is brought to 8 by adding sodium carbonate and the procedure of example 1 is followed. Already in 28 minutes equimolar amounts of alkali are consumed and only 5.71% 2-keto-D-gluconic acid is formed.
Example 4 pH=7

Use the same procedure as mentioned above but adjust the pH to 7.

TABLE 3

| pH | alkali | Time (min) | 2-keto-D-gluconic | unreacted prod. | selectivity |
|---|---|---|---|---|---|
| 7.00 | 100% | 47 | 18.0 | 78.0 | 81.9 |
|  | 120% | 107 | 34.7 | 56.5 | 79.6 |
|  | 129% | 167 | 38.9 | 47.7 | 74.3 |

100% alkali is equivalent to equimolar amounts of alkali compared to D-glucose.
Example 5 pH=6

Use the same procedure as above mentioned but adjust the pH to 6.

TABLE 4

| pH | alkali | Time (min) | 2-keto-D-gluconic | unreacted prod. | selectivity |
|---|---|---|---|---|---|
| 6.00 | 100% | 180 | 38.0 | 53.4 | 81.4 |
|  | 103% | 240 | 40.7 | 49.7 | 80.9 |
|  | 104% | 300 | 41.7 | 47.4 | 79.4 |
|  | 106% | 360 | 43.0 | 45.6 | 78.9 |

100% alkali is equivalent to equimolar amounts of alkali compared to D-glucose.
Example 6 pH=5

Use the same procedure as above mentioned but adjust the pH to 5.

TABLE 5

| pH | NaOH | Time (min) | 2-keto-D-gluconic | unreacted prod. | selectivity |
|---|---|---|---|---|---|
| 5.00 | 40% | 60 | 12.8 | 83.0 | 75.7 |
|  | 73% | 120 | 23.9 | 68.2 | 75.2 |
|  | 83% | 180 | 24.7 | 67.0 | 74.9 |
|  | 93% | 390 | 29.7 | 59.6 | 73.5 |
|  | 96% | 630 | 32.2 | 55.4 | 72.1 |

100% alkali is equivalent to equimolar amounts of alkali compared to D-glucose.

EXAMPLES 7–9

Catalytic Oxidation of D-glucose Starting at Different pH Levels

Preparation of catalyst

The catalyst Pt/Pb/C with ratio Pt/Pb=5/1 has been prepared according to the method described in example 1. 1.832 g lead (II) acetate $3H_2O$ is added to the suspension of 222.72 g Pt(5%)/C (44.9% d.s) in 200 ml cold demineralised water. The working-up is similar as described in example 1.

Catalytic Oxidation of D-glucose at Constant pH Compared with Oxidation at Decreasing pH Starting pH=8

The procedure of example 1 is repeated, but the catalyst prepared with Pt/Pb ratio of 5/1 is used. The pH is adjusted to 8 by sodium carbonate and equimolar amounts of sodium carbonate (0.4M) are consumed within 1 hour. The pH is then allowed to drop below 5.

Starting pH=7

A similar procedure is followed using the same catalyst (ratio Pt/Pb 5/1) but the starting level of the pH is 7 instead of 8. After 1 hour again the pH is dropped below 5.

Finally, the procedure of example 4 is followed with the catalyst Pt/Pb/C (ratio of Pt/Pb 5/1) and the pH is kept constant during the whole reaction.

The results are displayed in FIG. 1.

EXAMPLES 10–12

Catalytic Oxidation Using Catalysts With Different Pt/Pb Ratios

Three types of catalysts with different lead content are prepared:

Ratio of Pt/Pb=5/1.—results—Table 6.
Ratio of Pt/Pb=5/2.—results—Table 7.
Ratio of Pt/Pb=5/2.5—results—Table 8.

Reactions are performed as in Example 2, the pH is allowed to drop below 5.

TABLE 6

(ratio of Pt/Pb = 5/1)

| pH | Time (min) | 2-keto-D-gluconic | unreacted prod. | selectivity |
|---|---|---|---|---|
| 8.00 | 60 | 2.8 | 96.4 | 88.4 |
| 5.81 | 120 | 42.4 | 50.8 | 86.2 |
| 5.43 | 180 | 62.2 | 25.6 | 83.6 |
| 5.08 | 240 | 67.1 | 17.7 | 81.6 |
| 4.80 | 300 | 68.1 | 15.5 | 80.7 |
| 4.75 | 360 | 68.7 | 14.3 | 80.2 |

TABLE 7

(ratio of Pt/Pb = 5/2)

| pH | Time (min) | 2-keto-D-gluconic | unreacted prod. | selectivity |
|---|---|---|---|---|
| 8.00 | 60 | 3.3 | 95.4 | 72.7 |
| 7.01 | 120 | 28.6 | 67.9 | 89.0 |
| 5.22 | 180 | 68.6 | 21.8 | 87.7 |
| 4.94 | 240 | 72.6 | 16.6 | 87.0 |

TABLE 7-continued (ratio of Pt/Pb = 5/2)

| pH | Time (min) | 2-keto-D-gluconic | unreacted prod. | selectivity |
|---|---|---|---|---|
| 4.88 | 300 | 73.4 | 15.6 | 86.9 |
| 4.84 | 360 | 73.9 | 14.2 | 86.1 |

TABLE 8

(ratio of Pt/Pb = 5/2.5)

| pH | Time (min) | 2-keto-D-gluconic | unreacted prod. | selectivity |
|---|---|---|---|---|
| 8.00 | 50 | 5.1 | 94.9 | 100.00 |
| 5.21 | 120 | 62.4 | 27.6 | 86.1 |
| 4.96 | 180 | 68.2 | 20.6 | 85.9 |
| 4.86 | 240 | 69.7 | 18.5 | 85.5 |
| 4.80 | 300 | 69.9 | 17.6 | 84.8 |
| 4.72 | 360 | 72.0 | 14.8 | 84.5 |

EXAMPLE 13 (COMPARATIVE)

Catalytic Oxidation of D-gluconic Acid

D-gluconic acid was used as starting material 50.0 g of gluconolactone is dissolved in 950 ml demineralised water. The pH is adjusted to 6.0 with 25 g of a 45% w/w sodium hydroxide solution. The solution is heated to 55° C. under nitrogen, until no more oxygen is detected. 6.35 g of the prepared Pb/Pt/C catalyst (ratio Pt/Pb 5/2) is added and the suspension is stirred at 1300 rpm for another 10 minutes under nitrogen. The reaction is started by switching from nitrogen to oxygen (maximum 10% oxygen in the mixture). The reaction is continued without further pH control. The reaction is stopped after 2.5 hours reaction time.

TABLE 9

| Time (h) | pH | % residual gluconic acid | % 2-keto gluconic acid | % selectivity |
|---|---|---|---|---|
| 0 | 6.0 | 100 | 0 | |
| 0.5 | 5.8 | 41.7 | 55.2 | 94.7 |
| 1.0 | 5.6 | 20.7 | 74.3 | 93.7 |
| 1.5 | 5.2 | 10.0 | 83.0 | 92.2 |
| 2.0 | 5.0 | 8.7 | 83.2 | 91.1 |
| 2.5 | 5.0 | 7.9 | 83.7 | 90.9 |

EXAMPLE 14 (COMPARATIVE)

Oxidation of D-gluconic Acid at Constant pH=6

50.0 g of gluconolactone is dissolved in 950 ml demineralised water. The pH is adjusted to 6.0 with 25 g of a 45% wiw sodium hydroxide solution.The solution is heated to 55° C. under nitrogen, until no more oxygen is detected. 6.35 g of the prepared Pb/Pt/C catalyst (ratio Pt/Pb 5/2) is added and the suspension is stirred at 1300 rpm for another 10 minutes under nitrogen. The reaction is started by switching from nitrogen to oxygen (maximum 10% oxygen in the mixture). The pH is kept at 6.0 by controlled addition of 26 ml 0.4 M sodium carbonate. The reaction is stopped after 1.5 hours reaction time reaching a selectivity of 89.9%.

TABLE 10

| Time (h) | pH | % residual gluconic acid | % 2-keto gluconic acid | % selectivity |
|---|---|---|---|---|
| 0 | 6.0 | 100 | 0 | |
| 0.5 | 6.0 | 56.2 | 41.7 | 95.2 |
| 1.0 | 6.0 | 20.8 | 73.4 | 92.7 |
| 1.5 | 6.0 | 9.8 | 81.1 | 89.9 |

EXAMPLES 15–17 (COMPARATIVE)

Oxidation of D-gluconic Acid Starting at Different pH Values

Using D-gluconic acid

A similar procedure as Example 13 is repeated, with the catalyst Pt/Pb/C (ratio Pt/Pb 5/2). The pH is adjusted to 7.2 by sodium hydroxide. The pH is then allowed to drop to 5.1.

A similar procedure is followed with the same catalyst (ratio Pt/Pb 5/2) but the starting level of the pH is 6 instead of 7.2. The pH is dropped to pH 5.

Finally, the pH is adjusted to 5.0 by sodium hydroxide. The pH is then allowed to drop to 4.3.

The results are displayed in FIG. 2.

What we claim is:

1. A one-pot process for producing 2-keto-D-gluconic acid comprising:

oxidizing D-glucose with molecular oxygen in the presence of a platinum based catalyst doped with lead or bismuth, wherein the oxidizing is conducted in at least two stages, said stages comprising:

(a) in situ oxidizing D-glucose with molecular oxygen gas in the presence of said catalyst for such time as the reaction medium obtained is maintained at a constant pH value between 7 and 10 through the selected addition of a sufficient amount of alkali, relative to the D-glucose, until said alkali is consumed; and (b) continuing the oxidizing while allowing the pH to drop from a constant value to a pH value less than 6.

2. A process according to claim 1, wherein said alkali comprises a metal hydroxide or metal carbonate.

3. A process according to claim 1, wherein the alkali comprises sodium hydroxide, potassium hydroxide, or sodium carbonate.

4. A process according to claim 1, wherein the D-glucose comprises anhydrous D-glucose or D-glucose monohydrate.

5. A process according to claim 1, wherein the pH in (b) is allowed to drop to a pH of 5 or less.

6. A process according to claim 1, wherein the catalyst is prepared by precipitating lead salts onto a platinum-based catalyst, wherein the weight ratio of platinum to lead is 5:0.5 to 5:2.5.

7. A process according to claim 6, wherein the weight ratio of platinum to lead is 5:1.5 to 5:2.5.

8. A process according to claim 1, wherein the process is conducted at a temperature in the range of 400° C. to 70° C.

9. A process according to claim 1, wherein the process is conducted at a temperature in the range of 50° C. to 60° C.

10. A process according to claim 1, wherein in (a) the pH is a value within the range of 8 and 9.

11. A process according to claim 1, wherein (a) the alkali addition is approximately equivalent to the D-glucose.

12. A process for producing iso-ascorbic acid comprising:

producing 2-keto-D-gluconic acid by oxidizing a sugar comprised of D-glucose with molecular oxygen in the presence of a platinum-based catalyst doped with lead or bismuth, wherein said process in situ preparation of D-gluconic acid oxidizing D-glucose with molecular oxygen whereby a reaction medium is obtained, maintaining the pH of said reaction medium at a constant value between 7 and 10 by addition of an alkali, until all or near equimolar (?) amounts of said alkali are consumed, and thereafter continuing oxidation while permitting the pH to drop to a value less than 6, whereby the obtained 2-keto-D-gluconic acid is obtained; and converting the 2-keto-D-gluconic acid to iso-ascorbic acid.

* * * * *